United States Patent
Ruch et al.

(10) Patent No.: US 12,117,802 B2
(45) Date of Patent: Oct. 15, 2024

(54) CHARACTERIZING LIQUIDS BASED ON FEATURES EXTRACTED FROM TIME-DEPENDENT, DIFFERENTIAL SIGNAL MEASUREMENTS

(71) Applicant: International Business Machines Corporation, Armonk, NY (US)

(72) Inventors: Patrick Ruch, Pratval (CH); Gianmarco Gabrieli, Zurich (CH); Rui Hu, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 188 days.

(21) Appl. No.: 17/645,383

(22) Filed: Dec. 21, 2021

(65) Prior Publication Data

US 2023/0195079 A1    Jun. 22, 2023

(51) Int. Cl.
    *G16C 20/70*    (2019.01)
    *G05B 19/4155*  (2006.01)

(52) U.S. Cl.
    CPC ......... *G05B 19/4155* (2013.01); *G16C 20/70* (2019.02); *G05B 2219/40585* (2013.01)

(58) Field of Classification Search
    CPC ...... G05B 19/4155; G05B 2219/40585; G16C 20/70
    See application file for complete search history.

(56) References Cited

U.S. PATENT DOCUMENTS

| | | | |
|---|---|---|---|
| 3,807,222 A * | 4/1974 | Eggers | G01N 29/032 73/590 |
| 5,011,589 A | 4/1991 | Amemiya | |
| 5,284,568 A * | 2/1994 | Pace | G01N 27/403 204/403.03 |
| 6,290,838 B1 * | 9/2001 | Mifsud | G01N 33/18 422/534 |
| 6,520,010 B1 | 2/2003 | Bergveld | |

(Continued)

FOREIGN PATENT DOCUMENTS

| | | | | |
|---|---|---|---|---|
| CN | 109187392 A * | 1/2019 | | G01N 21/31 |
| WO | WO-2022053690 A1 * | 3/2022 | | |

OTHER PUBLICATIONS

Soldatkin (A.P. Soldatkin, "New enzyme potentiometric sensor for hypochlorite species detection", Sensors and Actuators B 43, 1997) (Year: 1997).*

(Continued)

*Primary Examiner* — Catherine T. Rastovski
*Assistant Examiner* — Yossef Korang-Beheshti
(74) *Attorney, Agent, or Firm* — Randy Tejeda

(57) ABSTRACT

One or more computer processors obtain one or more time-dependent signals with one or more sensor pairs in a sensing system, respectively, wherein each of the one or more time-dependent signals are obtained as a differential signal of a respective pair of the one or more sensor pairs by successively sensing a reference liquid and each liquid in a set of liquids to be characterized with the respective pair; extracting one or more sets of features from one or more portions of the one or more time-dependent signals, respectively, each of the one or more portions including a signal portion obtained while sensing each liquid in the set of liquids with said respective pair; and characterize each liquid in the set of liquids based on the one or more extracted sets of features.

25 Claims, 9 Drawing Sheets

(56) References Cited

U.S. PATENT DOCUMENTS

| | | | |
|---|---|---|---|
| 9,201,068 B2 | 12/2015 | Suni | |
| 2008/0086042 A1* | 4/2008 | Brister | A61B 5/6848 |
| | | | 600/347 |
| 2011/0208457 A1 | 8/2011 | Merz | |
| 2018/0144259 A1* | 5/2018 | Mansouri | G01N 35/00613 |
| 2019/0159703 A1* | 5/2019 | Aggarwal | A61B 5/7267 |
| 2020/0285983 A1* | 9/2020 | Bhattacharyya | G06N 20/10 |

OTHER PUBLICATIONS

Barycenter, www.merriam-webster.com/dictionary/barycenter (Year: 2024).*

Barycenter, www.dictionary.com/browse/barycentre (Year: 2024).*

Alegret, Slavador, "Application of a potentiometric electronic tongue as a classification tool in food analysis", Available online Feb. 24, 2005, DOI : 10.1016/j.talanta.2005.01.049, 8 pages.

Cole et al., "Development of Smart Tongue Devices for Measurement of Liquid Properties", Oct. 2004, 8 pages, <https://www.researchgate.net/publication/3431259>.

Cortina et al., "A sequential injection electronic tongue employing the transient response from potentiometric sensors for anion multidetermination", Published online: Jun. 24, 2006, DOI 10.1007/s00216-006-0530-2, 9 pages.

Duran et al., "Virtual Instrument for an Automated Potentiometric e-TongueEmploying the SIA Technique", Published: Dec. 15, 2005, DOI : 10.3390/s6010019, 11 pages.

Liu et al., "Electronic Tongue Recognition with Feature Specificity Enhancement", Published: Jan. 31, 2020, 13 pages, <https://www.ncbi.nlm.nih.gov/pmc/articles/PMC7038381/>.

Vlasov et al., Nonspecific Sensor Arrays ("Electronic Tongue") for Chemical Analysis of Liquids, (IUPAC Technical Report), © 2005 IUPAC, 19 pages, DOI: 10.1351/pac200577111965.

Gabrieli et al., "Quantification of Multi-Ion Mixtures Using a Machine Learning Assisted Integrated Electronic Tongue Leveraging Mobile and Cloud Platforms", Abstract Only, Published on May 30, 2021, Grace Period Disclosure, 5 pages, <https://ecs.confex.com/ecs/239/meetingapp.cgi/Paper/146200>.

* cited by examiner

CHARACTERIZING LIQUIDS BASED ON FEATURES EXTRACTED FROM TIME-DEPENDENT, DIFFERENTIAL SIGNAL MEASUREMENTS

STATEMENT REGARDING PRIOR DISCLOSURES BY THE INVENTOR OR A JOINT INVENTOR

The following disclosure(s) are submitted under 35 U.S.C. 102(b)(1)(A):

"Quantification of Multi-Ion Mixtures Using a Machine Learning Assisted Integrated Electronic Tongue Leveraging Mobile and Cloud Platforms". cs.confex.com/ecs/239/meetingapp.cgi/Paper/146200, was published on May 30, 2021, in the course of the 239th Electrochemical Society (ECS) Meeting and the 18th International Meeting on Chemical Sensors (IMCS), authored by Gianmarco Gabrieli, Rui Hu, and Patrick Ruch, all inventors of the present invention, as well as Keiji Matsumoto, Yuksel Temiz, Sacha Bissig, Ralph Heller, Antonio Lopez, Jorge Barroso Carmona, Kitahiro Kaneda, and Yasumitsu Orii.

BACKGROUND

The present invention relates generally to the field of liquid characterization, and more particularly to measuring differential signals by successively sensing a reference liquid and a target liquid.

Data-driven chemical sensors, such as potentiometric electronic tongues (PETs), are based on classification or prediction models, e.g., to determine concentrations of certain compounds in liquids. Such models require extensive training. Typically, PETs are used to provide a set of steady-state voltages, which are measured after equilibration of the PET with a sample liquid.

Some PETs are designed to provide multiple timeseries of voltage measurements of the liquid. An advantage is that more data can be extracted from the multiple timeseries and used to characterize the sample liquid. However, a major difficulty stems from the lack of defined protocol for the analysis of the timeseries to build a useful classification or prediction model.

SUMMARY

Some PETs are designed to provide multiple timeseries of voltage measurements of the liquid. An advantage is that more data can be extracted from the multiple timeseries and used to characterize the sample liquid. However, a major difficulty stems from the lack of defined protocol for the analysis of the timeseries to build a useful classification or prediction model.

According to a first aspect, the present invention is embodied as a method of characterizing liquids. The method relies on a sensing system that includes N sensors, where the sensors are arranged in n sensor pairs, where $N \geq 2$ and $n \geq 1$. Given a set of liquids including a reference liquid and m liquids to be characterized ($m \geq 2$), the method comprises, for each of the m liquids, obtaining time-dependent signals, extracting features from the time-dependent signals, and then characterizing the liquids based on the extracted features. More precisely, n time-dependent signals are obtained with the n sensor pairs, respectively, for each liquid of the m liquids. Each of the n time-dependent signals is obtained as a differential signal of a respective pair of the n sensor pairs by successively sensing the reference liquid and said each liquid with said respective pair. Moreover, for each liquid of the m liquids, n sets of k features ($k \geq 1$) are extracted from n portions of the n time-dependent signals, respectively. Each of the n portions includes a signal portion obtained while sensing said each liquid with said respective pair. Eventually, each liquid is characterized based on the n sets of k features extracted for this liquid. For example, each of the m liquids can be characterized so as to classify this liquid, or so as to perform quantitative predictions, i.e., quantify one or more properties of the liquids, such as ionic concentrations.

In embodiments, the extracted features include at least one transient feature. That is, the signal portion of each of the n time-dependent signals includes a transient signal response obtained due to a transition from sensing the reference liquid to sensing said each liquid with the respective pair of the n sensor pairs, and each of the n sets of k features extracted includes at least one transient feature.

Preferably, the signal portion of each of the n time-dependent signals further includes a steady-state signal response obtained at an end of the transient signal response. In that case, the feature extraction can be performed in such a way that each of the n sets of k features extracted further includes at least one steady-state feature.

In embodiments, the reference liquid is sensed again at each cycle, after having successively sensed the reference liquid and a target liquid. That is, each of the n time-dependent signals is obtained by further sensing the reference liquid again after having successively sensed the reference liquid and said each liquid with said respective pair. Thus, the signal portion of each of the n time-dependent signals includes a further transient signal response obtained due to a transition from sensing said each liquid to sensing said reference liquid again with the respective pair of the n sensor pairs. Accordingly, each of the n sets of k features extracted can advantageously include at least one further transient feature of the further transient signal response.

In preferred embodiments, the sensors are potentiometric sensors. Each of the n time-dependent signals is obtained as a differential, potentiometric signal. The N sensors may for instance be, designed, each, to electrochemically interact with each of the liquids. Preferably, the sensing system includes an array of the N sensors; the array is designed so as to allow said each liquid to be simultaneously sensed by the n sensor pairs. Thus, the n time-dependent signals are simultaneously obtained for said each liquid, by simultaneously sensing said each liquid with the n sensor pairs.

Preferably, the k features extracted from each of the n portions for said each liquid include two features, i.e., a feature obtained from a maximum voltage variation in the transient signal response, with respect to a reference value obtained by sensing the reference liquid with said respective pair, and a feature obtained from a slope of the transient signal response.

More preferably, the signal portion of each of the n time-dependent signals further includes a steady-state signal response obtained at an end of the transient signal response. In addition, each of the k features further includes, for said each liquid and for each of the n sets, three features. The latter are respectively obtained from: a final absolute voltage value of the steady-state signal response; a final relative voltage value of the steady-state signal response; and an average of a complete signal response with respect to said reference value. The complete signal response includes the transient signal response and the steady-state signal response.

In embodiments, the method further comprises selecting the reference liquid for it to be intermediate between the m liquids, with respect to one or more properties. Preferably, said one or more properties includes one or more voltage signal response values of the signal responses obtained with one or more of the n sensor pairs. The one or more voltage signal response values include one or more of a steady-state voltage signal response value, an average voltage signal response value, and a maximal voltage signal response value.

Preferably, the method further comprises, prior to selecting the reference liquid, obtaining n signal responses for each of the liquids of the set, including the reference liquid, though the latter is not identified as such yet. Still, the reference liquid can be selected based on the n signal responses obtained, prior to obtaining the n time-dependent signals for each of the m liquids.

In preferred embodiments, the number n of sensor pairs is equal to N−1, and the n pairs of sensors are designed such that each of the resulting n time-dependent signals is linearly independent of remaining ones of the n time-dependent signals.

In preferred embodiments, each of the m liquids is characterized so as to quantify ion concentrations in the liquid. More precisely, each of the m liquids is an aqueous mixture of ions and each of the m liquids is characterized so as to quantify concentrations of one or more ions therein.

In embodiments, each liquid is characterized using a cognitive model trained based on labelled examples, where each of the labelled examples includes n×k features, by feeding the n sets of k features obtained for said each liquid to the trained model for it to produce an inference, i.e., a classification or a prediction. The cognitive model may for instance include one or more regression models. Preferably, the cognitive model includes both a linear regression model and a nonlinear regression model.

According to another aspect, the invention is embodied as a system for characterizing liquids. The system comprises a liquid storage, a sensing system, and a processing system. The liquid storage includes liquid containers adapted for storing respective liquids. The liquids include a reference liquid and m liquids to be characterized, where m≥2. The sensing system has N sensors arranged in n sensor pairs, where N≥2 and n≥1, and where each of the n sensor pairs is configured to produce a differential signal, in operation. Moreover, the sensing system and the liquid storage system are jointly configured to allow the sensing system to perform m sensing cycles. In operation, during each of the m sensing cycles, each of the n sensor pairs successively senses the reference liquid and a respective one of the m liquids to be characterized, so as to obtain n time-dependent signals as differential signals for each liquid of the m liquids to be characterized. The processing system is connected to the sensing system to access the n time-dependent signals obtained, in operation. Consistently with the present methods, the processing system is further configured to extract, for said each liquid, n sets of k features from n portions of the n time-dependent signals accessed, respectively, where k≥1 and each of the n portions includes a signal portion obtained while sensing said each liquid with said respective pair, in operation. The processing system is further configured to characterize said each liquid based on the n sets of k features extracted for said each liquid.

Preferably, the sensing system comprises an array of the N sensors. The array is designed to allow the sensing system to simultaneously sense a liquid via the n sensor pairs, so as to simultaneously obtain the n time-dependent signals m at each of the m sensing cycles.

In embodiments, the sensing system comprises a device with a probe comprising the array of the N sensors, and a housing having an external surface, the latter including both a first surface portion and a second surface portion. The housing is designed to maintain the probe so as for the probe to protrude from the second surface portion and thereby extend outside the housing, opposite to the first surface portion, thereby defining a gap between the first surface portion of the housing and a portion of a lateral surface of the probe. The gap has an open end and a closed end, the latter defined by the second surface portion of the housing.

Preferably, the N sensors are potentiometric sensors, whereby each of the n time-dependent signals is obtained as a differential, potentiometric signal, in operation.

In preferred embodiments, the liquid storage is a turntable platform, adapted to rotate the containers in a plane, and the array is mounted on a linear displacement stage, adapted to move the array of the N sensors perpendicularly to that plane.

According to a final aspect, the invention is embodied as a computer program product for characterizing liquids. The computer program product comprises a computer readable storage medium having program instructions embodied therewith. The program instructions are executable by processing means to cause the latter to access, for each liquid of m liquids to be characterized, n representations of n time-dependent signals, respectively. Each of the n time-dependent signals is a differential signal of a respective pair of n sensor pairs of a sensing system. The differential signal is assumed to have been obtained by successively sensing a reference liquid and said each liquid with said respective pair. The program instructions further cause the processing means to identify n portions of the n time-dependent signals, where each of the n portions includes a signal portion that has been obtained while sensing said each liquid with said respective pair. This embodiment further causes the processing means to extract n sets of k features (k≥1) and characterize said each liquid based on the n sets of k features extracted therefor.

BRIEF DESCRIPTION OF THE DRAWINGS

FIG. 1A illustrates various components of the system, which includes a liquid storage configured as a turntable platform with liquid containers, a sensing system with an array of potentiometric sensors, and a processing system, in accordance with an embodiment of the present invention. FIGS. 1B and 1C illustrates the operation of the sensing system, in accordance with an embodiment of the present invention. The turntable platform is rotated to bring a given container in position (FIG. 1B) and the array of sensors is dipped into a liquid contained in this container for measuring properties of this liquid (FIG. 1C);

Figure 1A:
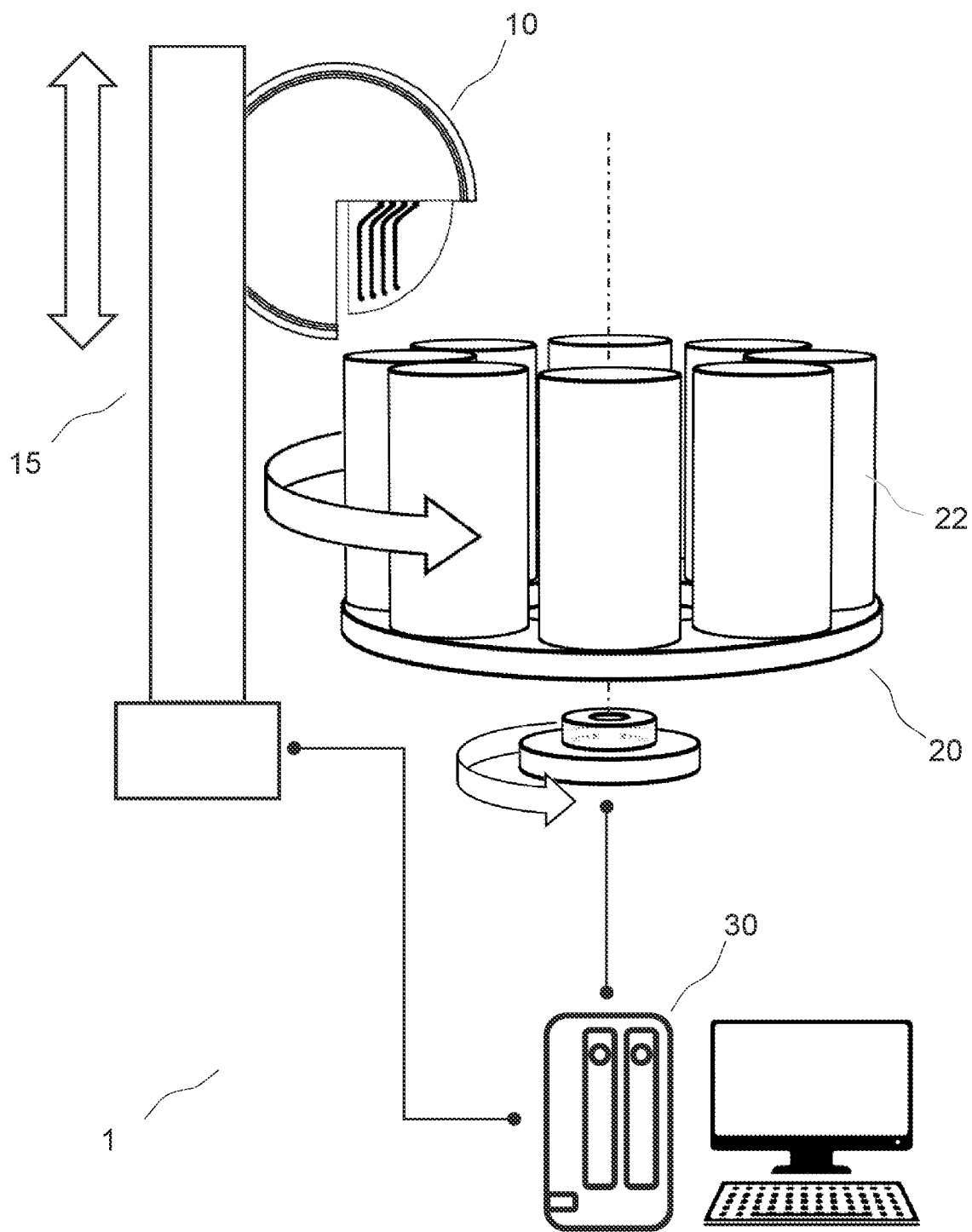
FIGS. 1A, 1B, and 1C (i.e., FIG.) are functional block diagrams illustrating a components of a system for characterizing liquids, in accordance with an embodiment of the present invention.

The accompanying drawings show simplified representations of systems, devices, and parts thereof, as involved in embodiments. Technical features depicted in the drawings are not necessarily to scale. Similar or functionally similar elements in the figures have been allocated the same numeral references, unless otherwise indicated.

DETAILED DESCRIPTION

The following description is structured as follows. General embodiments and high-level variants are described in section 1. Section 2 addresses particularly preferred embodiments; Section 3 concerns technical implementation details. Implementation of embodiments of the invention may take a variety of forms, and exemplary implementation details are discussed subsequently with reference to the Figures.

1. General Embodiments and High-Level Variants

A first aspect of the invention is now described in detail, in reference to FIGS. 1A-5 and 7. This aspect concerns a method of characterizing liquids. The present method and variants are collectively referred to as the "present methods". All references Sn refer to methods steps of the flowchart of FIG. 7, while numeral references pertain to physical parts or components of the devices and systems shown in FIGS. 1A-3 and 8.

Figure 1B:
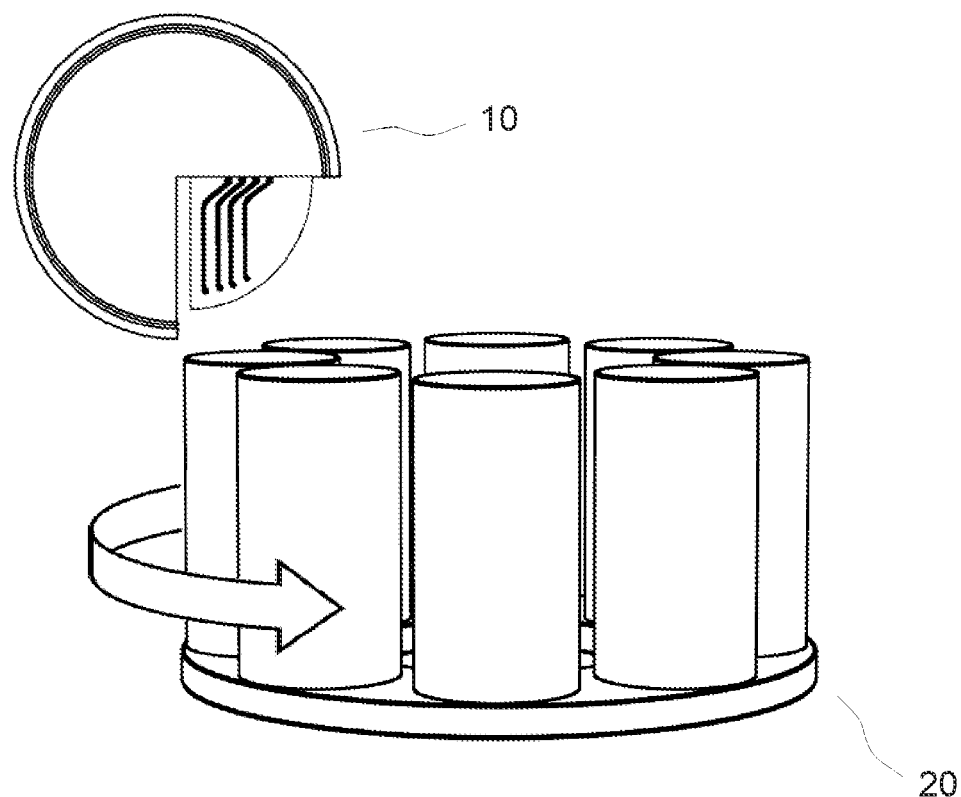
Figure 1C:
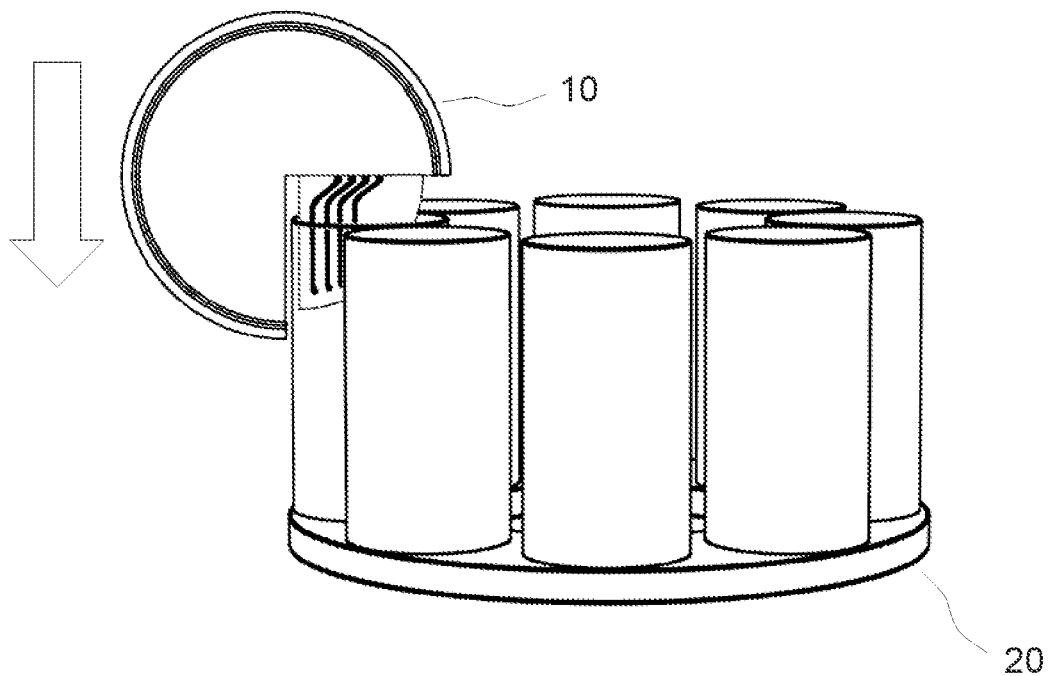
Figure 2:
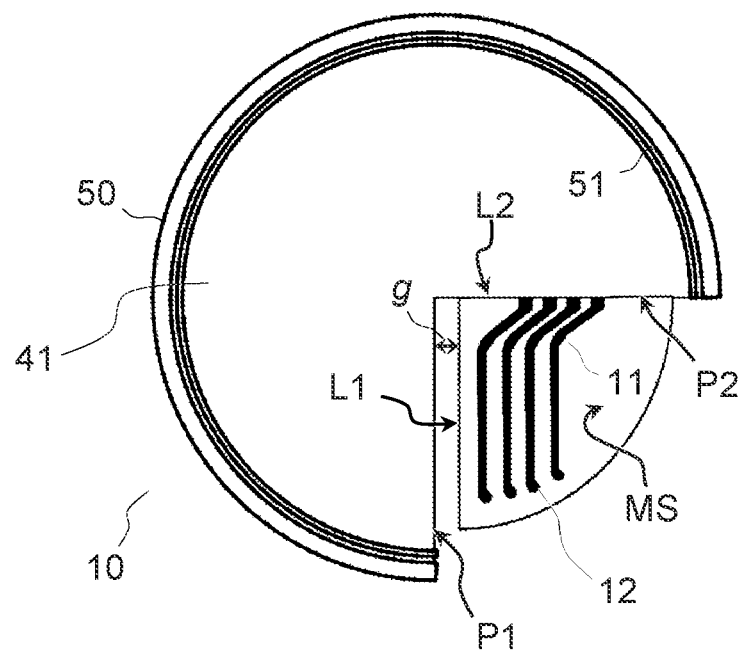
FIG. 2 is a diagram schematically illustrating a sensing system, as involved in embodiments. The sensing system includes a probe with an array of potentiometric sensors and a housing, shaped so as to define a gap between a surface of the housing and the probe, in accordance with an embodiment of the present invention.
Figure 3:
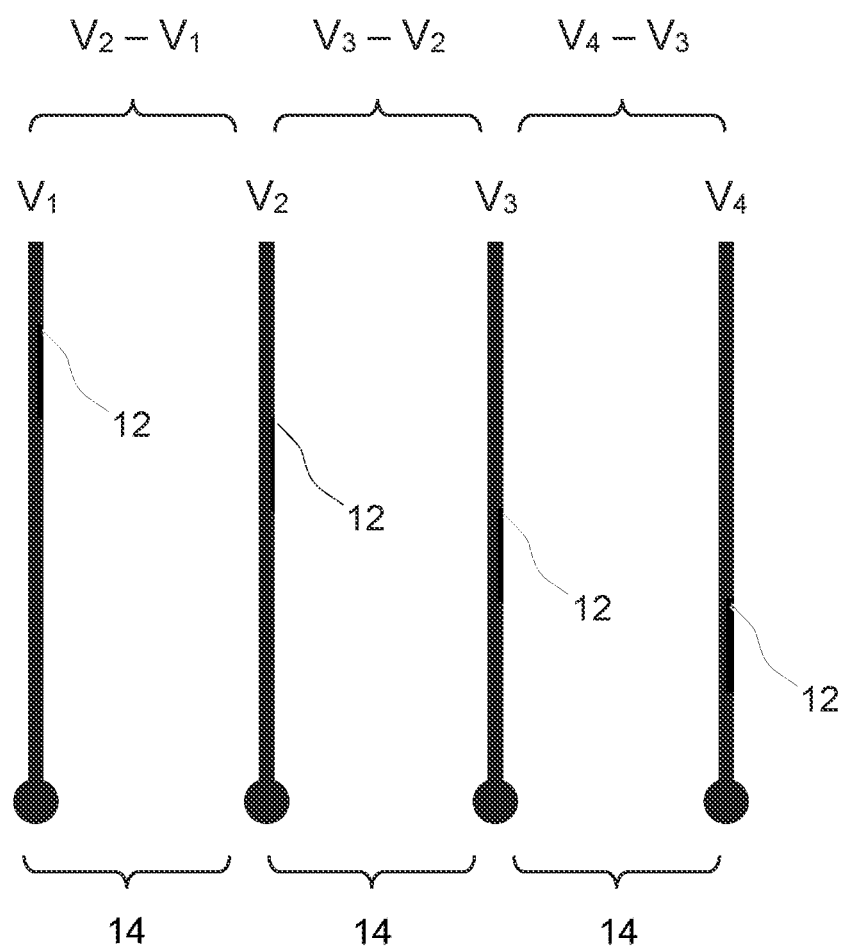
FIG. 3 is a diagram schematically depicting potentiometric sensors of a probe of a sensing system such as shown in FIG. 2 and illustrating how pairs of sensors can be selected to ensure linearly independent differential signals, in accordance with an embodiment of the present invention.

The method relies on a system 1 (i.e., present invention), which includes a sensing system 10, such as shown in FIGS. 1A-2. The sensing system 10 includes N sensors 12, which are arranged in n sensor pairs 14, as illustrated in FIG. 3. The number N of sensor must be larger than or equal to two (N≥2), so as to form at least one pair (n≥1). The N sensors 12 are typically designed to electrochemically interact with the test liquids. The sensor pairs are formed from the n sensors; the sensor pairs are used to obtain differential signals. In principle, any number of sensor pairs may be contemplated. In principle, the sensor pairs may be fully disconnected, partly connected, or fully connected, i.e., ⌈N/2⌉≤n≤N(N−1)/2). Preferably though, the maximal number of pairs of sensors considered is equal to N−1, so as to ensure linearly independent signals, as in embodiments described later. The sensing system 10 typically involves an array 11 of sensors 12 (e.g., potentiometric sensors), which are arranged so as to simultaneously sense a liquid, as in preferred embodiments.

The method further requires a set of liquids, which include a reference liquid and m liquids to be characterized, where m≥2. Several liquids are initially provided, see step S10 in FIG. 7. In embodiments, the reference liquid is already known as such, initially. In variants, the reference liquid may initially not already be identified as such. However, initial measurements may possibly be performed in order to select a suitable reference liquid among all the liquids initially provided.

Figure 7:
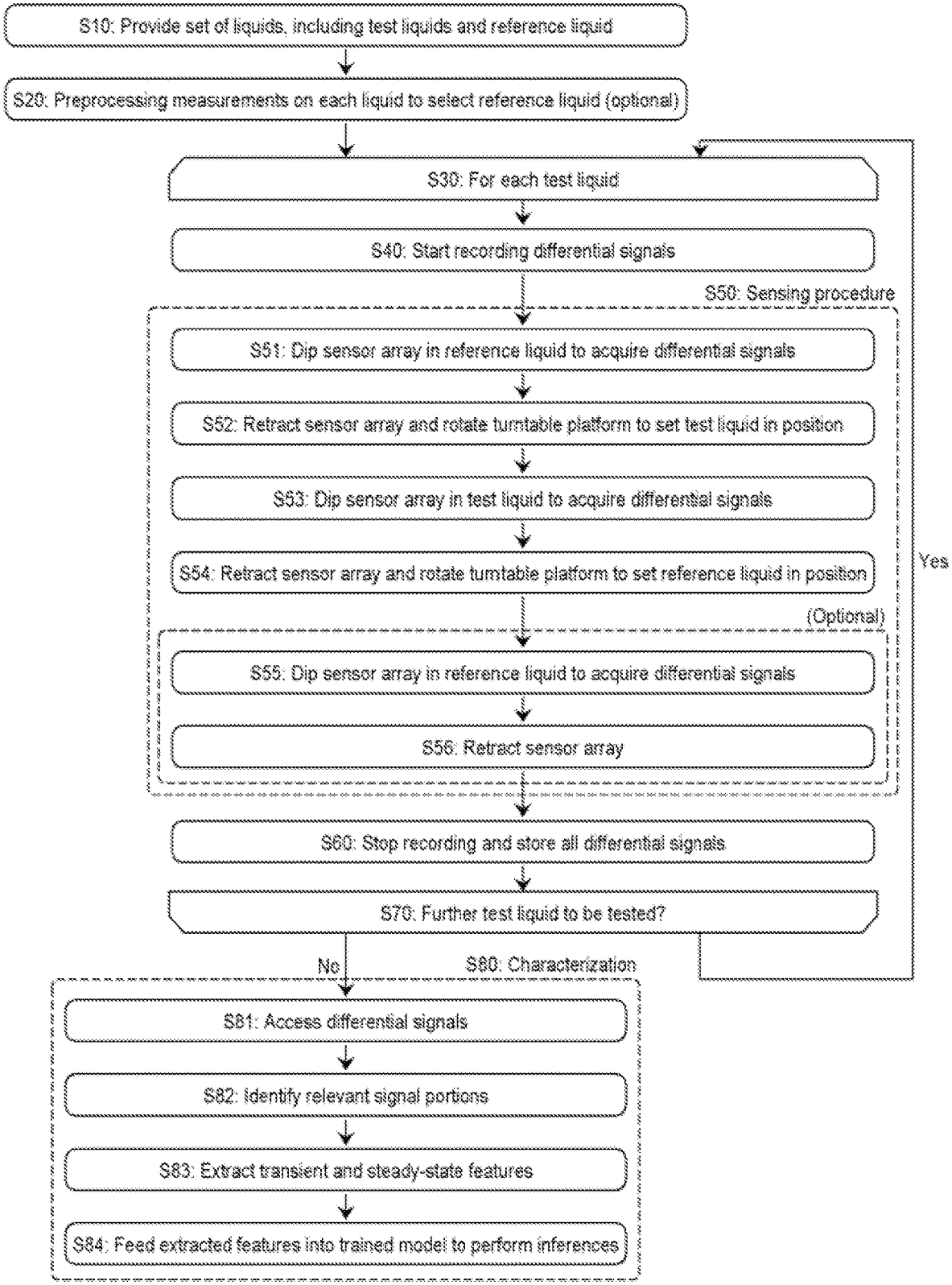
FIG. 7 is a flowchart depicting operational steps of a program, on a general purpose computerized system within the environment of FIG. 1, for characterizing liquids, in accordance with an embodiment of the present invention.

Several measurement steps are then performed, for each of the m liquids, as denoted by the loop/steps S30-S70 in FIG. 7. The m liquids are also referred to as "test liquids" in the following. That is, n time-dependent signals are obtained (step S50 in FIG. 7) with the n sensor pairs 14, respectively, for each of the m test liquids. Each of the n time-dependent signals is obtained as a differential signal, via a respective pair of the n sensor pairs 14. Importantly, each signal is obtained by successively sensing the reference liquid (step S51) and said each liquid (step S53) with a respective pair 14 of sensors 12.

Figure 4A:
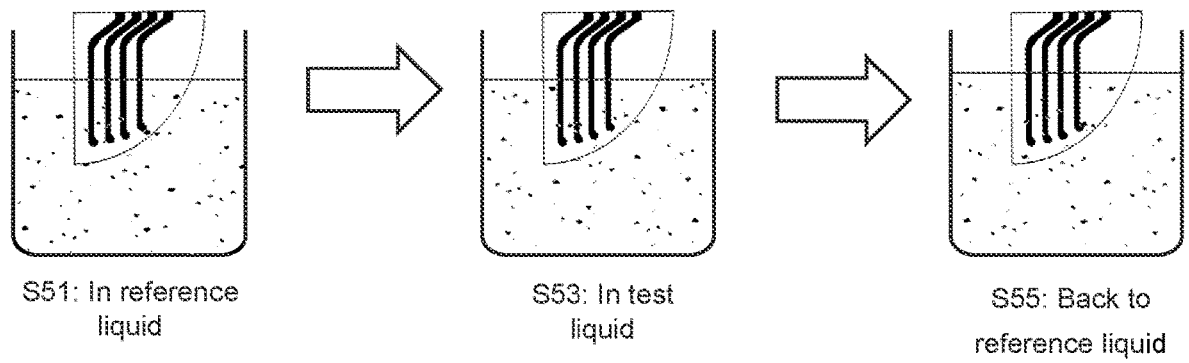
FIG. 4A is a diagram schematically illustrating the operation of a sensing system such as shown in FIG. 2, where the probe of the device is used to successively sense a reference liquid, a target liquid, and then the reference liquid again, in accordance with an embodiment of the present invention.
Figure 4B:
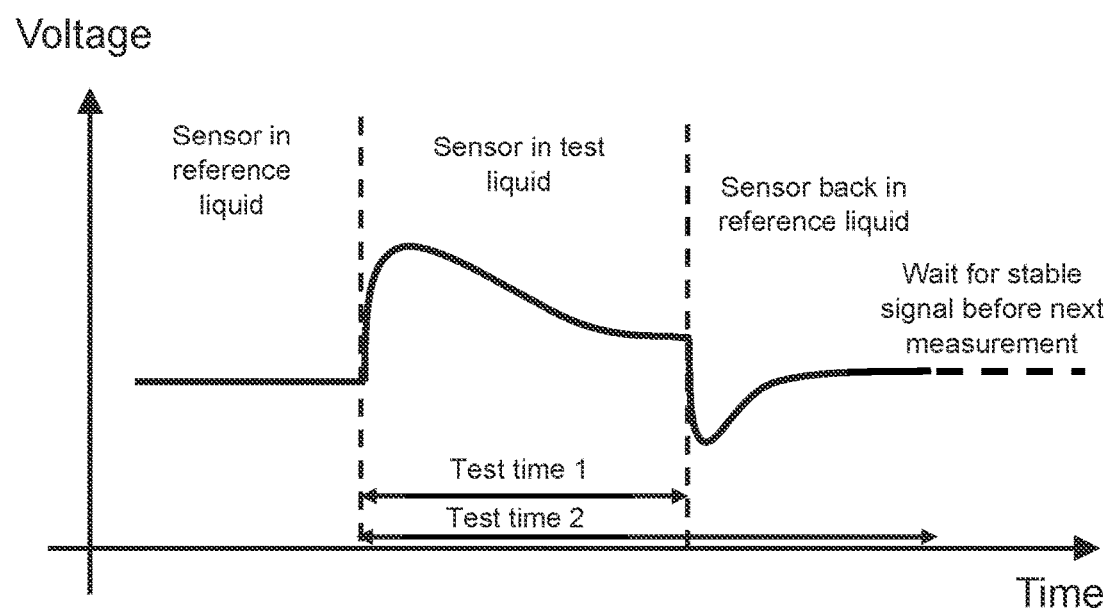
FIG. 4B is a graph that schematically represents a curve corresponding to a time-dependent differential signal (voltage), as typically obtained by sensing liquids as in FIG. 4A, in accordance with an embodiment of the present invention.
Figure 5:
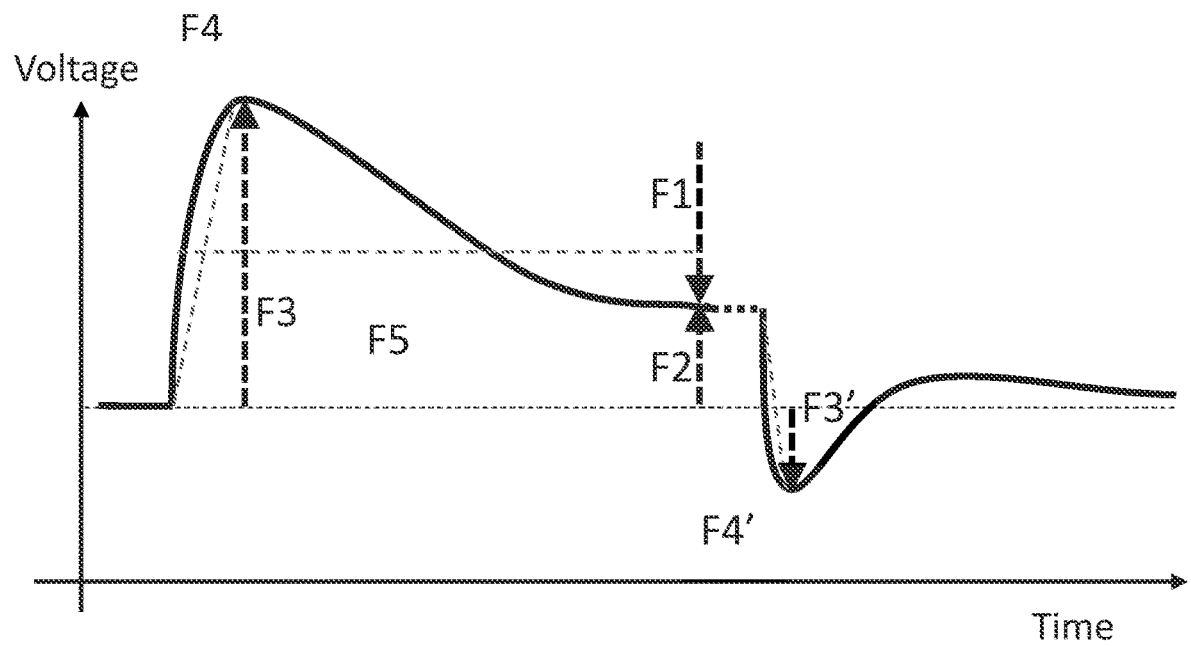
FIG. 5 is a diagram schematically depicting features of a time-dependent differential signal such as shown in FIG. 4B, which features are meant to be extracted and fed into a cognitive model, as in embodiments, in accordance with an embodiment of the present invention.

Next, the present invention (e.g., sensing system 10) extracts features from the n time-dependent signals and, this, for each of the m test liquids. More precisely, one set of features are extracted from a portion of each of the time-dependent signals. In other words, n sets of k features are extracted (step S83) from n portions of the n time-dependent signals, respectively. Each of the n sets includes at least one feature (i.e., k≥1). Moreover, each of the n signal portions considered for feature extraction includes a signal portion obtained while sensing each test liquid of the m liquids, i.e., such a signal portion includes a portion of a time-dependent differential signal obtained with a respective sensor pair during the sensing of a test liquid, i.e., after having sensed the reference liquid. Each signal portion typically starts at a point in time corresponding to the transition to a test liquid. In embodiments, the signal portion effectively considered for feature extraction corresponds to the sole time period ("Test time 1" in FIG. 4B), during which the test liquid is sensed, even though each time-dependent signal is obtained by successively sensing the reference liquid (step S51) and a test liquid (step S53). In that case, the signal portion considered is a portion such as delimited by the vertical dashed lines in FIG. 4B. In variants, the signal portion considered for feature extraction corresponds to the period "Test time 2" in FIG. 4B, i.e., it additionally include the last portion on the right hand side (RHS) of FIG. 4B, corresponding to a period during which the reference liquid is sensed again. An example of such a signal portion is shown in FIG. 5, together with features to be extracted. In all cases, the signal portion considered for feature extraction includes transient features. The relevant signal portions are identified at step S82 in FIG. 7, e.g., by computing derivatives and identifying both singularities and flat portions of the corresponding curves. In an embodiment, the raw differential signals typically exhibit additional fluctuations due to transition periods during which the sensor transits though the air.

Such oscillations, however, can easily be removed during a preprocessing step. The signals shown in FIGS. 4B and 5 are assumed to have been rid of such fluctuations Eventually, each test liquid is characterized (step S84) based on the n sets of k features extracted from relevant portions of the n time-dependent signals obtained for this liquid. The characterization step (step S84) typically aims at classifying this liquid or quantifying one or more properties of this liquid (i.e., performing a quantitative prediction for this liquid), using any appropriate computerized procedure, preferably based on a model such as a cognitive model.

According to the proposed approach, the sensing system is used to successively sense a reference liquid and a test liquid, which one wants to characterize. In embodiments, the reference liquid may be sensed again at each cycle, i.e., after having sensed the test liquid, as illustrated in FIG. 4A. In an embodiment, the sensing system 10 includes an array 11 of the N sensors 12, as illustrated in FIGS. 2, 3, and 4A. Such an array 11 can sense each liquid by immersing the array 11 in that liquid, whereby each liquid is simultaneously sensed by the n sensor pairs 14 and the n time-dependent signals are simultaneously obtained in step S50 for each liquid. Each measurement on a test liquid must be preceded by an immersion of the sensor array 11 in the reference liquid, as depicted in FIG. 4A. In addition, each measurement on a test liquid can possibly be followed by an immersion of the sensor array 11 in the reference liquid, as also depicted in FIG. 4A. Such sensing cycles are repeated for each test liquid of the set of m liquids considered for characterization.

The proposed approach relies on differential signals, which has advantages over absolute measurements, especially in terms of drifting and stability of the obtained signal responses. Typically, the data are continuously recorded by each sensor pair and at each measurement cycle corresponding to each test liquid. In practice, the differential signals obtained via the sensor pairs are typically sampled to form timeseries, prior to processing the data (e.g., to extract features). In an embodiment, some preprocessing may be needed, e.g., to clean the signal values and remove fluctuations, if necessary. Each readout describes the time evolution of each differential signal obtained via a respective pair of sensors, i.e., from sensing the reference liquid to sensing the test liquid, and, if necessary, sensing the reference liquid again, as illustrated in FIGS. 4A and 4B.

In an embodiment, only a portion of the readout is effectively exploited to extract features, see FIG. 5. However, this portion includes transient features. As explained above, this portion corresponds to a differential signal obtained after having started to sense the test liquid, i.e., after switching from sensing the reference liquid to sensing the test liquid. Thus, information on test liquids can be extracted also from the transient responses of the sensor pairs 14, corresponding to the transition from the reference liquid to the test liquid and, this, for each test liquid. And as indicated earlier, the exploited portion may possibly include a further transient response, corresponding to the time period during which the reference liquid is being sensed again (FIG. 4A, RHS). Thus, one or two transient responses of the sensor pairs 14 may be exploited.

In other words, the present approach takes into account signal variations occurring after switching liquids, i.e., after switching from the reference liquid to the test liquid and, possibly, after switching back from the test liquid to the reference liquid. As a result, the signal portion exploited to extract features includes transient features. Preferably, the signal portion considered for each of the differential signals starts at a transition point and extends to a point where it reaches a stable equilibrium signal. Thus, it may effectively include a combination of transient and steady-state signal features. In embodiments, both transient and steady-state signal features are extracted to characterize the liquids.

The features extracted may advantageously include transient features F3, F4 such as shown in FIG. 5. In this example, a signal portion is identified (step S82) for a given differential signal (with a respective sensor pair), where this signal portion includes a transient signal response (FIG. 4B, center), obtained due to the transition from the reference liquid (FIG. 4A, LHS) to a test liquid (FIG. 4A, center). Thus, the features extracted from this portion may include one or more transient features F3, F4, as illustrated in FIG. 5. Similarly, each of the n sets of k features extracted may include one or more transient features F3, F4.

In embodiments, additional information is extracted also from the transient responses corresponding to the transition back from the test liquid to the reference liquid, as illustrated in FIG. 5. That is, each of the n time-dependent signals is obtained by further sensing (step S55) the reference liquid again after having successively sensed (steps S51 and S53) the reference liquid and a test liquid. For example, the sensor pairs 14 are first moved from the reference liquid to the test liquid and, after a given testing time, are moved back into the reference liquid. Thus, the signal portion exploited for each of the n differential signals may be enlarged to include a further transient signal response obtained due to the transition back from the test liquid to the reference liquid. In that case, one may advantageously extract additional transient features from the further transient signal response, i.e., each of the n sets of k features extracted further includes at least one further transient feature F3', F4' as illustrated in FIG. 5.

Notwithstanding, steady-state features may possibly be exploited too, in addition to transient features such as described above. That is, the signal portion considered for each of the n differential signals may further include a steady-state signal response, as obtained at the end of the first transient signal response (to the end of the measurement on the test liquid, FIG. 4A, center). Thus, each of the n sets of k features extracted may possibly include one or more steady-state features F1, F2 of the test liquids, as illustrated in FIG. 5. The steady-state readout value(s) in the reference liquid is normally not needed as it is not descriptive of any of the test liquids.

As illustrated above, the present approach makes it possible to extract features from a timeseries that includes transient values, instead of exploiting the final (steady-state) readout values only. Moreover, the extracted features may possibly include transient features pertaining to two transitions, instead of only one. Still, steady-state features of the test liquid measurements may advantageously be extracted too and added to the transient features, to enrich the datasets and eventually improve the characterization. So, in embodiments, the extracted features include transient features pertaining to two transitions, as well as steady-state features obtained for the test liquid measurement.

Another aspect of the invention concerns a characterization system 1, which exploits the above concept to improve the overall performances of sensing systems, such as portable potentiometric electronic tongues (PETs). This system 1 and the protocol used in the present methods can be simply tuned for different applications by suitably selecting the reference liquid, e.g., by modifying the reference liquid composition. The reference liquid can notably be chosen based on properties of the other liquids (the test liquids), so as to optimize the dynamic range of the sensing system. The proposed approach allows faster measurements and improves the ability to discriminate between different types of compounds in the liquid samples, using simple detection means, which can be used by non-specialists, in the field.

This approach further allows a simpler calibration procedure compared to prior art methods. No multi-point calibration is required in the present case because the reference liquid used during the measurements serves as an intrinsic standard, i.e., measurement referencing is done based on the reference liquid only. Thus, no reference sensor (e.g., reference electrode) is required. For example, differential voltages can be measured between any pair of electrodes on the sensor array 11.

Moreover, the proposed approach can be used to obtain a fast indication of the sensor state-of-health; the sensor signals obtained with the reference liquid can easily be analyzed to provide information as to the state-of-health of the sensors.

It is preferred to use potentiometric sensors 12. A potentiometric signal measures a potential difference, i.e., with a potentiometric sensor, the interaction with a liquid under test produces a voltage variation. Performing sensing cycles as described above with potentiometric sensors makes it possible to set a reference condition on the sensors before each test liquid measurement and to extract additional information based on the way in which the active/sensing materials of the sensors react, starting from a same state. Similarly, the interaction with the reference liquid may differ depending on the final state of the sensors after sensing each test liquid. Using potentiometric sensors 12, the proposed approach allows reliable, faster, and more accurate measurements to be performed, e.g., with a portable device, without requiring any reference electrode, and further supports correction of short and long-term sensors drift.

In FIGS. 2 and 3, the sensors 12 are potentiometric sensors 12, i.e., electrodes in that case. Each of the n time-dependent signals is obtained (steps S51, S53, and S55 in FIG. 7) as a differential, potentiometric signal. The potentiometric signal measures a potential difference between the signals obtained via the two sensors 12 of each pair 14. A typical voltage perturbation, caused by the interaction between the sensors 12 and a test liquid, is the result of complex and mixed phenomena occurring at the interface between the sensing materials and the dissolved analytes. Common potentiometric sensors are based on sensitive active membranes that interact with chemical elements. The signal response depends on the state of each sensor before the interaction with each test liquid. Similarly, the interaction with a reference liquid after a specified testing time provides an additional contribution to the fingerprinting of a specific test liquid.

In variants to potentiometric signals, voltametric signals are exploited. In that case, a current is measured as the potential is varied. In other variants, the sensors are colorimetric sensors. In further variants, optical sensors are used. In fact, several types of transducers may be contemplated, provided that the sensor outputs can be converted to electrical signals. Preferred, however, is to rely on potentiometric signals, as assumed in the following.

In FIG. 5, the k features extracted (step S83) from each signal portion and for each test liquid include two transient features F3 and F4. The feature F3 corresponds to the maximum voltage variation in the transient signal response of the test liquid, with respect to the reference value obtained by sensing (step S51) the reference liquid with the same sensor pair. This reference value corresponds to the horizontal dashed line in FIG. 5. Thus, F3 corresponds to the maximal signal height with respect to the dashed line, as indicated by the corresponding vertical arrow. The feature F4 is obtained from the slope of the transient signal response, i.e., after the transition, as indicated by the curved arrow. As the present invention demonstrates, using such features F3, F4 can efficiently discriminate between liquids as said features do essentially not depend on the testing time. Such features notably provide adequate features for training a cognitive model. Additional transient features may possibly include the height of the inflection point before the maximum, and/or intermediate slopes around this point, for example.

In embodiments, the extracted features further include steady-state features of the signal response of the test liquid. That is, the signal portion exploited for each of the n time-dependent signals further includes, in step S82, the steady-state signal response obtained at the end of the transient signal response of the test liquid, which makes it possible to extract additional features. In particular, three types of features F1, F2, F5 of the steady-state signal response can be usefully exploited. These include the final absolute voltage value F1, see FIG. 5. The feature F1 is measured with respect to the zero voltage and is indicated by a vertical arrow. Another useful feature is the final relative voltage value F2, which is measured with respect to the reference value defined earlier. In an embodiment, use can also be made of an average F5 of the complete signal response, including the transient signal response and the steady-state signal response, as measured with respect to the reference value.

These additional types of features F1, F2, F5 are added to the transient features F3, F4 described earlier, making up five types of features in total. In embodiments, only the five types of features above are used, i.e., k=5. Because n sensor pairs are used to acquire n differential signal, this means that k×n=5 n features are extracted from measurements corresponding to each test liquid. In variants, however, further features are relied on, such as transient features F3', F4' seen in FIG. 5, which correspond to features extracted from the transient signal response obtained after switching back to the reference liquid, i.e., features F3', F4' correspond to the maximum voltage variation in the next transient signal response (with respect to the reference value) and the slope of the next transient signal response, respectively. In both cases, the number of features considered remains rather small (5 or 7 features for each time-dependent signal).

Such an approach is more reliable than approaches based on steady-state values only. It is also much more effective than blind machine learning extractions using all data points as input, which result in a very high-dimensional feature space and require a much more complex training. In other words, it is preferred to extract a limited number of signals features, albeit physically meaningful. Importantly, the feature extraction discussed above should be distinguished from automatic feature extractions performed by extraction layers of trained neural networks. In the present case, some feature engineering is performed, resulting in selected features F1-F5 (and, possibly, F3', F4'), which subtend a physically meaningful representation of the physically relevant signal portions of the differential signals obtained. However, relying on features F1-F5 (and, possibly, F3', F4') extracted as described above does not preclude the use of additional layers of feature extraction/dimension reduction. I.e., the total number l×n of features extracted (l=5 or 7 in the examples above) gives rise to l×n-dimensional vectors, which can be fed as input to a cognitive model, where the latter may possibly transform the input vectors into higher/ lower-dimensional vectors, with a view to performing inferences via further layers. So, in the present embodiments, use is made of engineered features, extracted from the differential signals, where the extracted features are physically meaningful features. Doing so provides better results than blind extractions and because less features are used compared to models using all data points as input, this simplifies the training (or, more generally, the parameterization) of the model and requires less computational resources on inferencing.

The following describes preferred protocols used to select or identify the reference liquid. The reference liquid is preferably selected (step S20) to be "intermediate" between the m liquids, so as to optimize the dynamic range of the differential signals obtained. In an embodiment, "intermediate" means that one or more properties of the reference liquid lie at intermediate positions between corresponding properties expected for the test liquids, such as chemical (e.g., composition) and/or physical (e.g., electrical) properties. Various properties may be considered, for example, ionic concentrations, the maximal signal response (absolute or relative), and/or the average steady-state signal response.

While such properties will normally be measurable properties, said properties do not necessarily need to be measured in practice. Indeed, often a priori knowledge is available on the class of liquids to be tested in practice, such that the reference liquid can be selected a priori. In such cases, the reference liquid is chosen based on known properties thereof, by comparing such properties to expected properties of the test liquids. Choosing an intermediate reference liquid results in maximizing the dynamic range of the signals obtained with the sensor pairs 14. Moreover, the choice of the reference liquid may affect the discrimination capabilities of the sensors, and consequently the prediction results. When the reference liquid has intermediate properties (e.g., an intermediate composition) within the range of test liquids, their separation can be maximized.

In an embodiment, the reference liquid can further be chosen to minimize the time required for equilibration of the potentiometric response, decreasing the measurement times and, thus, the overall processing time, while the specific features extracted from the dynamic evolution of the differential signals also contribute to decrease the processing time, compared with blind extraction methods. When the sensor is moved from the reference liquid to the test liquid, it reacts to establish a new equilibrium and, similarly, when it is moved back in the reference liquid it tends to restore its previous condition. The lower the perturbation affecting the sensing materials, the faster said perturbations reach the potential equilibrium, hence a further benefit of choosing an "intermediate" reference liquid. To that aim, the present invention may for instance try to select a reference liquid that is similar to the tested liquids, a priori, to obtain faster and more reliable responses. This, of course, assumes prior knowledge of the liquids to be tested. When the class of liquids to be tested is known, it is fairly easy to select a suitable reference liquid, a priori.

However, this may not always be the case in practice. There, a protocol is needed for adequately selecting a reference liquid when no prior knowledge exists for the liquids to be tested. Such a protocol would be useful to apply for the present approach to any use case. It may further be useful to identify a best reference liquid among several potential reference liquids, also when the class of test liquids is known, a priori. Ideally, this protocol should be more reliable and easier to implement than a mere trial-and-error process, not require a cumbersome, preliminary experimentation phase, and not assume knowledge of the chemical composition of the sample liquids.

A particularly simple protocol is to select the reference liquid out of the set of liquids initially provided, by measuring properties of all the liquids provided, due to the sensors available. In variants, the present invention may add one or more potential candidates for reference liquids to the test set and then measure properties of all the liquids available, including the candidate liquids. The added liquids may for instance include liquids that are typically used as reference liquids, according to experience gained with prior experiments. In other variants, an ad hoc reference liquid is created by mixing up two or more of all the liquids to be tested. In the latter case, it is typically not necessary to measure properties of the available liquids, prior to starting the sensing cycles, since the ad hoc liquid can be assumed to be a suitable reference liquid.

In other cases, though, the reference liquid can be identified by measuring properties of all the liquids provided, thanks to the available sensors. When such sensors are potentiometric sensors, such properties may for instance include specific signal response values, which are obtained (step S20) during preprocessing steps with one or more of the n sensor pairs 14. The signal response values may for instance include steady-state voltage signal response values, average values, and/or maximal (absolute or relative) voltage signal response values. Such values are determined by analyzing the differential signals obtained, using known mathematical procedures. The reference liquid is preferably selected as the liquid providing the most "intermediate" property or properties, e.g., the most centric steady-state value.

Various heuristics are utilized, for example, steady-state values obtained for each liquid and each sensor pair are compared to determine which liquid is the closest to the barycenter of all steady-state values and, this, for each type of signal obtained with each sensor pair. Then, the reference liquid can for instance be selected thanks to a majority vote. In variants, one may for instance seek to straightforwardly identify the liquid having steady-state values that minimize the distances to all other values for all types of differential signals combined. Many other heuristics can similarly be devised.

In an embodiment, in variants to steady-state values, the present invention may also identify the reference liquid based on maximal (absolute or relative) response values or the average response values obtained from any or each of the sensor pairs 14. However, the principle remains the same as with steady-state values, i.e., the reference liquid is identified as the liquid having the most intermediate values. The average voltage values are obtained by averaging signal responses from the curves produced by exposing the sensor pairs 14 to the compared liquids.

The protocols described above in respect of the reference liquid selection assume that the reference liquid is selected beforehand. That is, the preprocessing steps S20 are performed to select the reference liquid, prior to the sensing cycles, as in FIG. 7. To that aim, the present invention may, for instance, obtain (step S20) n signal responses for each of the liquids of the initial set, including the reference liquid, even though the latter is not identified as such yet. Then, the reference liquid is selected based on the n signal responses obtained, as described above.

In more complicated variants, the reference liquid is selected a posteriori, i.e., after the sensing cycles (step S50). This, however, requires considering any pair of liquids and successively sense any such pair at step S50, which considerably lengthens the procedure. Thus, it is preferred to select the reference liquid a priori, thanks to preliminary sensing step S20.

In general, the present invention seeks to minimize the number of differential signals, by suitably choosing the sensor pairs. A physically meaningful way of selecting the sensor pairs is to choose the sensor pairs so as for the resulting signals to be linearly independent. That is, the n pairs of sensors 12 are chosen such that each of the resulting n time-dependent signals is linearly independent of all the other signals. Now, given N sensors, the maximal number $n_{max}$ of such sensor pairs is equal to $n_{max}=N-1$. In order to maximize the number of differential signals (to maximize the number of subsequently extracted features), one may thus construct $n=n_{max}$ sensor pairs, in such a way that none of the resulting n time-dependent signals corresponds to a linear combination of remaining ones of the n time-dependent signals, as illustrated below.

For example, assumes that only four sensors 12 are available, as in the simple example of FIG. 3. In operation, such sensors produce signals $V_1$, $V_2$, $V_3$, and $V_4$. So, the present invention may select the pairs as those partly disconnected pairs that produce differential signals that cannot be obtained through linear combinations of the other signals. A possibility is to choose $V_{12}=V_1-V_2$, $V_{23}=V_2-V_3$, and $V_{34}=V_3-V_4$. However, differential signals such as $V_{13}=V_1-V_3$, $V_{14}=V_1-V_4$, and $V_{24}=V_2-V_4$ should not be considered in that case as said differential signals would result in physically redundant features, i.e., more than can be justified by the physical data. Indeed, $V_{13}$ should, in principle, be the same as $V_{12}+V_{23}$ and thus does not provide any additional information, i.e., $V_{13}$ can be formulated as a linear combination of $V_{12}$ and $V_{23}$. Therefore, measuring $V_{13}$ is not required if $V_{12}$ and $V_{23}$ are already being measured. Similarly, $V_{14}=V_{12}+V_{23}+V_{34}$ and $V_{24}=V_{23}+V_{34}$ should preferably be discarded. Thus, it is sufficient to rely on $\{V_{12}, V_{23}, V_{34}\}$ only. In an embodiment, this solution is not unique; other linearly independent triplets can similarly be identified. In any such case, however, the maximal number of linearly independent signals amounts to $N-1=3$. More generally, given N sensors, the present invention may want to connect $n=N-1$ sensor pairs and accordingly exploit $n=N-1$ differential signals. In embodiments, the sensor pairs are configurable. That is, the sensing system may be designed so as to allow a user to configure each pair.

The above example makes use of N−1 sensor pairs, which are partly connected, one pair after the other. That is, $V_{12}$ is partly connected to $V_{23}$ via $V_2$. Similarly, $V_{23}$ is partly connected to $V_{34}$ via $V_3$. In variants, however, the sensor pairs may be fully disconnected. In that case, given N sensors, the maximal number of sensor pairs is equal to $\lceil N/2 \rceil$. In other variants, the present invention may first acquire $N(N-1)/2$ signals corresponding to all the sensor pairs, select N−1 sensor pairs as linearly independent pairs, but average out signals obtained from the pairs. For example, in the previous example, the present invention may for example average the signals $V_{13}$ and $V_{12}+V_{23}$, which should in principle be the same, to form an effective signal $V_{eff,13}=(V_{13}+V_{12}+V_{23})/2$. Thus, $N(N-1)/2$ sensor pairs would be exploited in this case. Doing so, however, lengthens the procedure. So, it is preferred to rely on N−1 sensor pairs only, which is, in principle, sufficient and avoid redundant information.

The signals are typically stored (step S60) after each measurement (step S50). Once all relevant signals have been obtained in step S50, the relevant signal portions are identified (step S82), with a view to extracting (step S83) all the desired features F1-F5, F3', and F4'. The latter can then be fed as input to a computerized procedure, e.g., based on an analytical function, a statistical model, or a cognitive model. Preferred is to rely on a trained cognitive model, using the extracted features as input to perform inferences (step S84). For example, each of the m liquids can be classified (step S84), i.e., as a liquid belonging to one class or the other (e.g., genuine, non-genuine). Such an approach can for instance be used to detect counterfeits. In more sophisticated approaches, the cognitive model is trained to quantify one or more properties of the liquid, i.e., to make quantitative predictions. That is, each of the m liquids can be characterized (step S84) so as for the model to infer (step S84) one or more properties of the liquids, as exemplified below.

Figure 6:
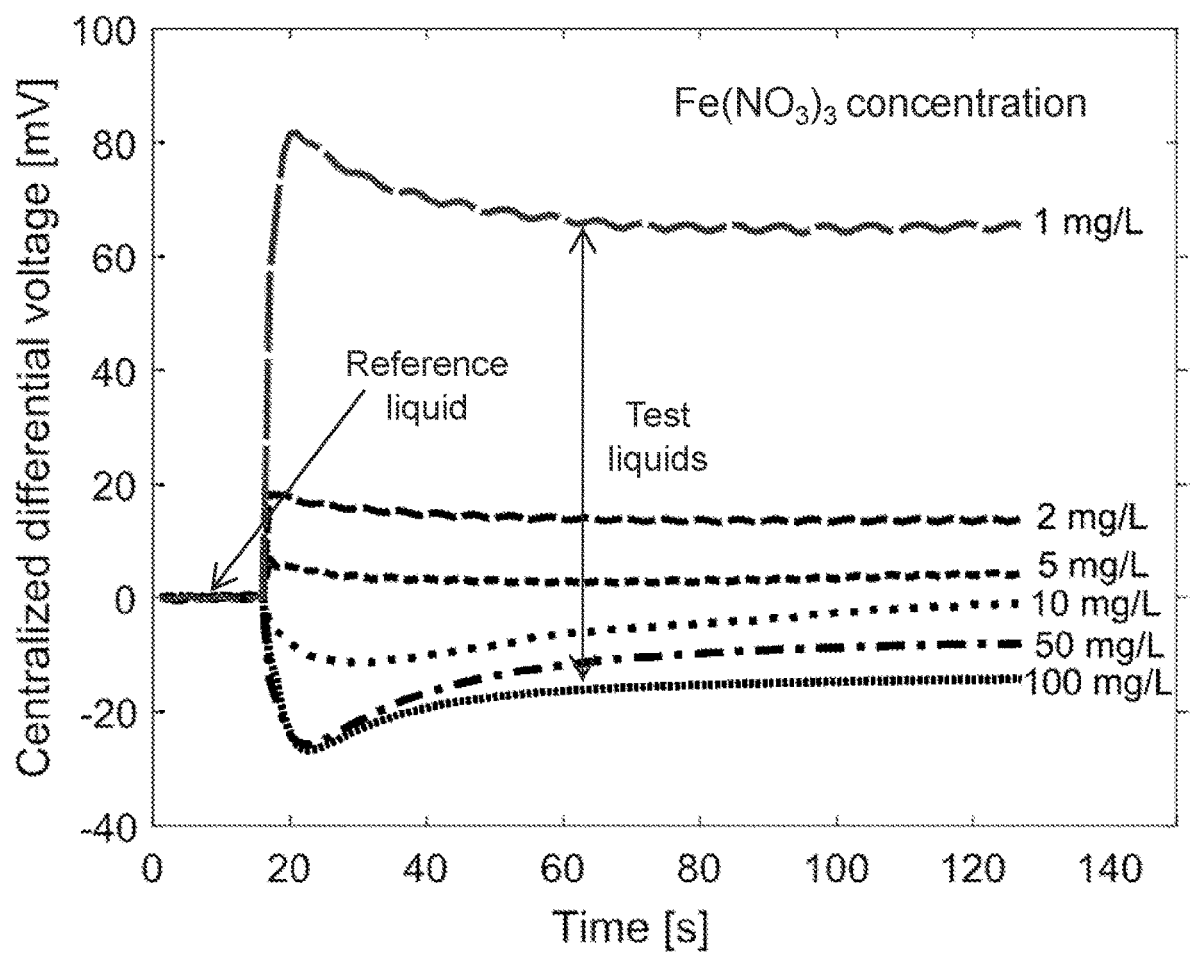
FIG. 6 is a graph illustrating an example of application, in accordance with an embodiment of the present invention. Differential signals are obtained with a given sensor pair, for various liquids having different concentrations of $Fe(NO_3)_3$. The aim is to characterize such concentrations thanks to features extracted from differential signals obtained via several sensor pairs, including the signals corresponding to the curves shown in FIG. 6.

For example, the present approach may be used to predict ionic concentrations in liquids, as in the example of FIG. 6. In this example, the reference liquid has been selected (step S20) to exhibit intermediate voltage values, so as to maximize the range of voltage values obtained for the test liquids compared to the voltage excursion between reference liquid and each test liquid. Each curve shown in FIG. 6 is a centralized signal; the zero value corresponds to the steady-state value obtained with the reference liquid at the end of step S51. In this example, the test liquids are solutions that include different concentrations of $Fe(NO_3)_3$. The curves shown correspond to signals obtained with a given sensor pair. These curves make it possible, together with curves obtained from additional sensor pairs, to quantify (step S84) the concentrations of $Fe(NO_3)_3$ compounds, where complex cations $Fe^{3+}$ are coordinated with nitrate anions. Features extracted from signal portions such as shown in FIG. 6 are fed to an adequately trained model to perform inferences as to the corresponding liquids, as discussed in more detail in section 2. In variants, the present approach can also be applied to liquid matrices, which may possibly include powders and/or any kind of particles (e.g., solute particles that do not dissolve in the solvent), with a view to classifying test liquids or predict properties such as concentrations of the solute particles, density, etc.

As evoked above, each test liquid is preferably characterized using a cognitive model. Such a cognitive model can initially be trained based on labelled examples of liquids having known properties. Such liquids are referred to as training liquids, for the sake of distinction. That is, each of the labelled examples including n×k features, extracted from the training liquids. The n sets of k features obtained for each training liquid are fed to the model to train the latter, based on the labels associated to the examples, as known per se. Later, during the inference phase, the n sets of k features obtained for each test liquid are fed to the model for it to produce an inference. As said, the inference can be a classification (e.g., of a class of liquid) or a or quantitative prediction (e.g., of a property of each test liquid). In embodiments, the cognitive model includes one or more regression models. It may for instance include both a linear regression model and a nonlinear regression model. In that case, two cognitive models are actually involved, including a multiple linear regression model and an extremely randomized trees model, for reasons that will become apparent in section 2.

Referring to FIGS. 1-3, and 8, another aspect of the invention is now described, which concerns a system 1 for characterizing liquids. As seen in FIGS. 1A, 1B, and 1C, the system 1 includes a liquid storage, which has several liquid containers 22 (e.g., vials), meant to store respective liquids. In operation, liquids are poured in the containers 22. Such liquids include a reference liquid and m liquids to be characterized (m≥2), referred to as test liquids. The reference liquid may not already be known as such yet, as discussed earlier.

The system 1 further includes a sensing system 10. Consistently with the present methods, the sensing system includes N sensors 12, e.g., potentiometric sensors, which are arranged in n sensor pairs 14, where N≥2 and n≥1. As explained earlier, each of the n sensor pairs 14 is configured to produce a differential signal, in operation.

The sensing system 10 incorporates a liquid storage system used to sense liquids, with a view to characterizing the m test liquids. Namely, the sensing system 10 and the liquid storage system are jointly configured to allow the sensing system to perform m sensing cycles. In operation of the characterization system 1, each sensor pair 14 successively senses the reference liquid and a respective test liquid during each sensing cycles, to obtain n time-dependent signals as differential signals for each test liquid. If necessary, each sensing cycle may further includes sensing the reference liquid again. The characterization system may further be used to perform preprocessing steps S20 as described earlier, if necessary.

Figure 8:
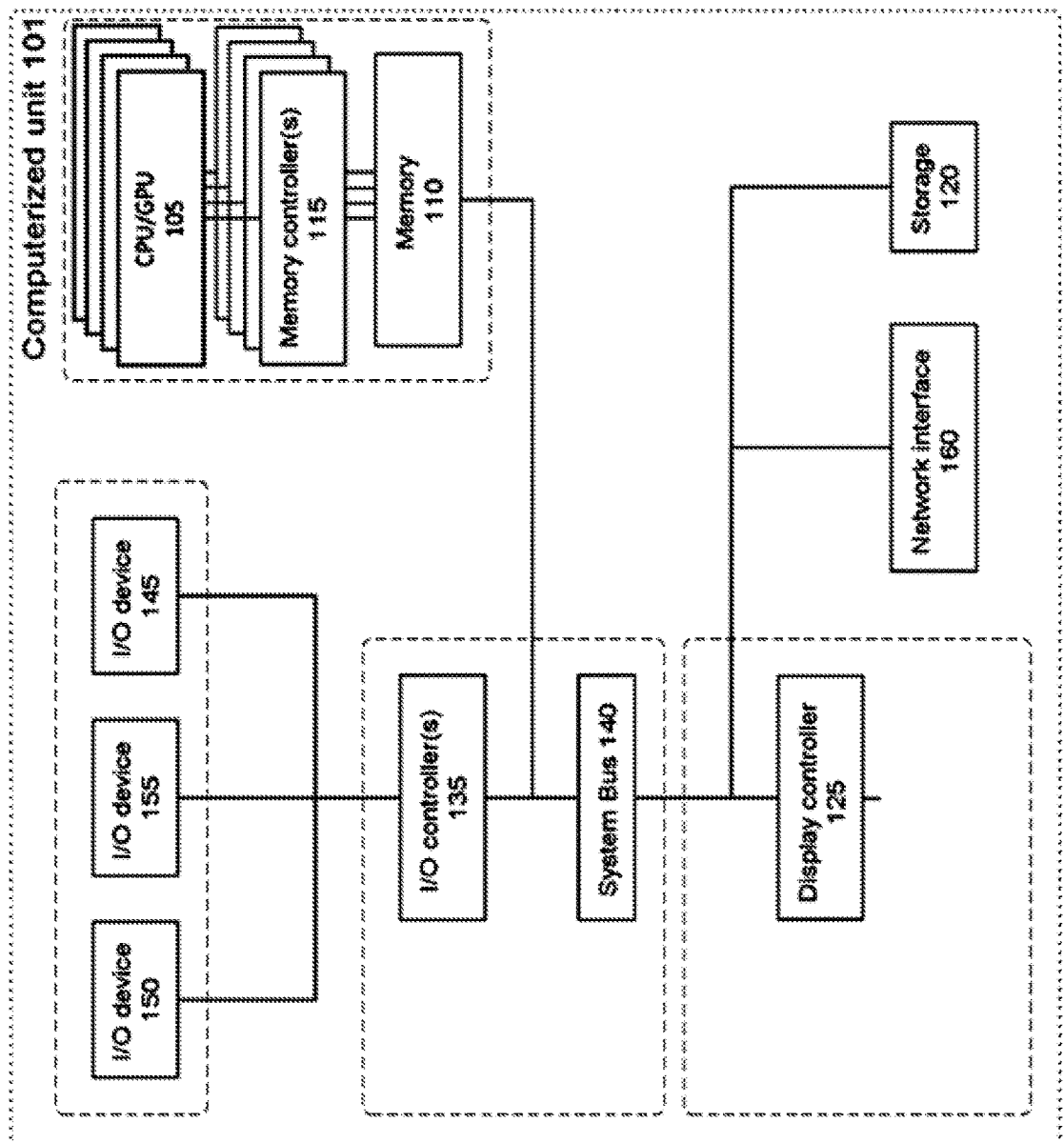
FIG. 8 is a block diagram of components of a general purpose computerized system, in accordance with an embodiment of the present invention.

The system 1 further includes a processing system 30, i.e., a computerized system, which is connected to the sensing system 10. The processing system 30 can accordingly access the n time-dependent signals obtained, in order to extract features from the signals and characterize the test liquids. The processing system 30 may for instance include a computerized unit 101 such as shown in FIG. 8, which is described in detail in section 3. Consistently with principles explained earlier in reference to the present methods, the processing system 30 is configured to extract, for each test liquid, n sets of k features from n portions of the n time-dependent signals accessed, respectively, where k≥1. As explained earlier, each of the n portions includes a signal portion corresponding to signal obtained while sensing each test liquid with a respective pair of sensors. The processing system 30 can then characterize each test liquid based on the corresponding n×k extracted features. Such features preferably include both transient and steady-state features, as discussed earlier in detail. More generally, the system 1 can notably be designed so as to perform steps according to any of the present methods.

In preferred embodiments, the sensing system 10 includes an array 11 of N sensors 12, such as depicted in FIGS. 2, 3, and 4A. This array 11 allows the sensing system 10 to simultaneously sense a liquid via the n sensor pairs 14, e.g., by dipping the array 11 in a corresponding container 22. This makes it possible to simultaneously obtain the n time-dependent signals m at each of the m sensing cycles.

The sensing system 10 includes a probe with an array 11 of sensors 12, as well as a housing 41. The latter has an external surface, which includes both a first surface portion P1 and a second surface portion P2. This housing is designed to maintain the probe, so as for the latter to protrude from the second surface portion P2 and thereby extend outside the housing 41, opposite to the first surface portion P1. This defines a gap g between the first surface portion P1 of the housing 41 and a portion L1 of a lateral surface of the probe, as best seen in FIG. 2. The gap g has an open end and a closed end, the latter defined by the second surface portion P2 of the housing. Such a design results in a compact, integrated multi-sensor package, which can conveniently be self-supported on a rim of a container due to the gap g, as illustrated in FIG. 1C. A particularly preferred sensing system 10 is described in detail in section 2.

Preferably, the sensors 12 are potentiometric sensors. Thus, each of the n time-dependent signals is obtained as a differential, potentiometric signal, in operation. The N sensors 12 may for instance be non-specific polymeric sensors. Suitable materials for sensors notably include conductive polymers (e.g., polypyrene, poly(3,4-ethylenedioxythiophene), polyaniline and variants thereof). In variants, such sensors may include metals, such as Pt, Au, Rh, Jr, and alloys thereof, and chalcogenides, among other examples.

The sensing system shown in FIG. 2 can advantageously be used with a preferred liquid storage such as depicted in FIGS. 1A, 1B, and 1C. The liquid storage includes a turntable platform 20, which is adapted to rotate the containers 22 in a plane. Meanwhile, the sensing system (including the array 11 of sensors) can be mounted on a linear displacement stage 15. The latter is designed to move the sensing system perpendicularly to the plane in which the containers are rotated, in operation. This way, the containers 22 can easily be set in position by rotating the turntable platform 20. Then the sensing system is dipped in steps S51, S53, and S55 into that container to sense a liquid therein, and retracted in steps S52, S54, and S56. These operations are performed to successively sense the reference liquid and a test liquid, and then the reference liquid again, if necessary. Moreover, such operations are repeated in steps S70 and S30 for each test liquid, as described earlier in reference to FIG. 7. A detailed description of FIG. 7 is provided in section 2.

Next, according to a final aspect, the invention can be embodied as a computer program product for characterizing liquids. The computer program product comprises a computer readable storage medium having program instructions embodied therewith. The program instructions are executable by processing means of a processing system such as the system 30 seen in FIG. 1A, which may include one or more computerized units 101 such as shown in FIG. 8.

The program instructions cause the processing means to take steps as described earlier in reference to the present methods and systems 1. Namely, such instructions causes the underlying processing system 30 to access representations of signals, for each test liquid. In operation, the signals are time-dependent differential signals obtained thanks to respective sensor pairs 14, as described earlier. Each differential signal is assumed to have been obtained by successively sensing a reference liquid and a test liquid with a respective sensor pair. The program instructions cause the processing means to identify relevant portions of the time-dependent signals, where each portion includes a signal portion that has been obtained while sensing said each test liquid with a respective sensor pair. Then, features are extracted, and the test liquid is accordingly characterized. In an embodiment, the features are typically extracted first, for all test liquids (through one at a time) and then successively fed to an appropriate model, such as a statistical model (i.e., a parameterized function) or, preferably, a cognitive model, as described earlier. Further detail as to computerized units and computer program products are provided in section 3.

The above embodiments have been succinctly described in reference to the accompanying drawings and may accommodate a number of variants. Several combinations of the above features may be contemplated. Examples are given in the next section.

2. Specific Embodiments

2.1 Preferred Sensing Systems

Preferred sensing systems 10 are designed as portable sensors. Such a sensor basically comprises a probe and a housing, which may include multiple parts 41, 50, 51. The probe comprises a sensing part 11, i.e., an array of sensors 12. The sensing part 11 notably shows a lateral surface. A first portion of the lateral surface of the sensing part 11 is denoted by reference L1, see FIG. 2. The probe is preferably designed as an essentially planar substrate, thus having two opposite base surfaces MS linked by said lateral surface (only one of these base surfaces MS is visible in FIG. 2). The substrate may have any suitable shape, such that the lateral surface show distinct surface portions L1, L2. The sensors 12 may notably be arranged on one of the base surfaces MS of the substrate, as in FIG. 2, or on each base surfaces MS. In variants, the sensors 12 may possibly be provided within the substrate, or otherwise attached to a body of the probe. In other variants, the sensing part may be structured to define one or more flow paths leading to the sensors. The flow path(s) may for example be formed by patterned structures (such as microfluidic channels), and/or a wicking medium (like a fibrous/porous medium such as paper or a nitrocellulosic material), to guide the liquid towards the sensors, which may be arranged in any suitable place in the sensing system.

In embodiments, the sensors 12 are electrodes. In general, the sensors 12 may possibly comprise polymeric membranes (comprising ionophores), conductive and/or insulating polymers, chalcogenide glasses, noble metals (such as Pt, Au, and Ru) and/or ignoble metals (also called anodic metals or corroding metals, such as Ni, Fe, and Ti), carbonaceous materials (such as graphitic carbon, activated carbon, diamond-like carbon, and/or graphene), etc.

The housing 41, 50, 51 has an external surface, which notably includes a first surface portion P1 and a second surface portion P2, see FIG. 2. The housing 41, 50, 51 is generally designed to maintain the probe in such a manner that the sensing part 11 of the probe protrudes from the second surface portion P2, see FIG. 2. The probe thus extends (at least partly) outside the housing 41, 50, 51, opposite to said first surface portion P1, i.e., a portion L1 of the lateral surface of the sensing part 11 of the probe extends opposite to the surface portion P1 of the external surface of the housing.

As the probe protrudes from the second surface portion P2 of the housing 41, 50, 51, a gap g can be provided between the first surface portion P1 of the housing 41, 50, 51 and the lateral surface portion L1 of the probe, as best seen in FIG. 2. And as further seen in FIG. 2, the gap g has an open end (at the bottom of the sensing part 11 of the probe, in the orientation of FIG. 2). The opposite end (on top in FIG. 2) of the gap is closed by the second surface portion P2 of the housing 41, 50, 51. In other words, the gap g compares to a (rather long) notch. The lateral surface L1 of the sensing part 11 preferably extends parallel to said first surface portion P1 (subject to backlash), though this is not strictly needed.

Due to the open-ended gap g, a portable sensor as described above can be placed on a liquid container 22, such as a vial, a drinking glass, or a beaker, and so as to slot onto the rim of the container 22, i.e., the rim inserts in the gap, though its open end. This way, the sensors 12 of the probe can dip in a liquid in the container 22, in operation, see FIG. 1C. The gap g is typically between 1 and 5 mm, preferably less than 4 mm, or even less. More generally, the gap may be designed so as to slot the sensor onto any container of interest. This advantageously allows hands-free (i.e., self-supported) measurements.

In addition, this gap makes it possible to easily prevent other components (other than the sensing part 11 of the probe) to contact the liquid. Thus, the proposed design eases the operation of the sensor, which is furthermore easy to service in the field. Accordingly, the proposed design improves the reliability and the reproducibility of the measurements performed with the sensor compared to conventional portable sensors. Such a sensor can notably be embodied as a compact, integrated multi-sensor package, self-supporting on a rim of a container. In particularly advantageous embodiments, the portable sensor may be designed as a kit of parts, mounted in a few seconds, without any fastening means such as threads, adhesives, or the like, i.e., just by assembling the parts 11, 40, 50, 51 together.

2.2 Preferred Flow of Operation

A preferred flow in shown in FIG. 7. First, a set of liquids are provided at step S10 and poured in respective containers 22. The liquids include test liquids and a reference liquid, although the latter may not already be identified as such yet. In that case, a series of preprocessing measurements are performed at step S20, on each of the liquids. The reference liquid is identified as being the most intermediate liquid, based on its measured properties (e.g., steady-state values of voltage differential signals acquired with potentiometric sensors 12). The container corresponding to this reference liquid is then selected and memorized, with a view to performing subsequent operations. Then, a series of measurements are performed (step S30) for each test liquid, i.e., the liquids to be characterized. The turntable platform 20 is rotated to bring the container 22 containing the reference liquid in position. The array 11 of sensor is still retracted at this point, as illustrated in FIG. 1B. At step S40, the sensing system starts recording differential signals and the sensing procedure (step S50) starts. At step S51, the sensor array is dipped in the reference liquid, thanks to the motorized stage 15, see FIG. 1A, to acquire differential signals pertaining to the reference liquid. At step S52, the sensor array is retracted (as in FIG. 1C) and the turntable platform 20 is rotated to set the container containing a first test liquid in position. The sensor array 11 is then dipped (step S53) in that test liquid to acquire differential signals. At step S54, the sensor array is retracted, and the turntable platform rotated to set the reference liquid in position. At this point, the sensing system may stop recording (step S60) and store all differential signals, before starting a new cycle, steps S70 and S30, in respect of another test liquid. Preferred, however, is to dip (step S55) the sensor array in the reference liquid again to complete measurements for the current test liquid. This makes it possible to obtain a further transient signal after switching from the current test liquid to the reference liquid. The sensor array is subsequently retracted, step S56, and the sensing system stops recording and stores all differential signals, step S60. Then, another cycle is started (decision step S70: Yes). This repeats until no more test liquid remains to be tested (decision step S70: No). Next, characterization (step S80) can be started. To that aim, the processing system 30 accesses (step S81) the differential signals as stored (the latter could also be kept in the main memory only), to identify (step S82) relevant signal portions and extract (step S83) both transient and steady-state features from such portions. The extracted features are eventually fed (step S84) into a suitably trained model for it to perform inferences, i.e., classifications or predictions.

2.3 Detailed Example of Application

An example of application is the direct quantification of multiple ions in aqueous mixtures. This is achieved by combining an automated machine learning pipeline with transient potentiometric data obtained from a single miniaturized array 11 of polymeric sensors 12 electrodeposited on a conventional printed circuit board. The sensing system includes 16 polymeric sensors to record transient differential voltages produced by the sensors 12 when transitioning from a reference solution to each test solution. The reference liquid obviates the need for a conventional reference electrode, as explained in section 1. Features are extracted from the transient signal portions and fed to a cognitive model. The latter involves a tree-based regression model, trained to infer concentrations of various metal cations in pure solutions. The inference takes less than 2 minutes.

In more detail, two different cognitive models are used for the quantification. The first model is a multiple linear regression (MLR) model, while the second model comprises extremely randomized trees (Extra Trees). The multivariate regression models were trained based on labelled sets of features to quantify ion concentrations. First, a multivariate standard calibration method, MLR, is applied as a baseline assuming a linear relation between the logarithm of the target ion concentration and the features extracted from the differential voltages. A multi-variate linear function is then built to model this relation. Second, a decision tree-based method is applied to explore non-linear mapping of features to target concentrations. The Extra-Trees algorithm can learn robust models by training over a large number of randomized trees constructed from sub-datasets. The accuracy of predicting the target ion concentration is estimated using leave-one-test-out (LOTO) and leave one-mixture-out (LOMO) cross-validation. LOTO corresponds to leave-one-out cross-validation on a given set of test solutions, whereby repeated measurements of the same test solution appear in both the test dataset and the training dataset. In LOMO, all repeated measurements for a given test solution are allocated to the test dataset, while the training dataset comprises all measurements performed on other solutions. A it turns out, LOMO provides a more rigorous cross-validation method, as the test solution represents a concentration unseen in the training dataset. The metrics used to define the accuracy of concentration prediction are the Mean Absolute Error (MAE) and the Mean Relative Error (MRE). In other words, the MRE for concentration estimation is used to assess which polymeric sensors, measurement features, and regression model are favored for the simultaneous quantification of the target cations in aqueous solutions.

In a model mixture comprising Al, Cu, Na and Fe, the mean relative error was found to depend on the type of ion. It varies between 1% for Fe and 44% for Na in the concentration range 1-10 mg/L. Overall, a mean relative error of 16% was obtained for quantification of these four ions across a total of 124 tests in different solutions spanning concentrations between 2-360 mg/L. Such results demonstrate how the analytical capability of a multi-selective sensor array 11 can leverage a data-driven approach through training by examples for accelerated testing and can be proposed to complement traditional analytical tools to meet industrial demands, including traceability of chemicals.

The present invention was tested in respect of other applications, such as the detection of low manganese (Mn) content in an electrolyte solution containing 5 mg/L of iron (Fe), using a potentiometric electronic tongue comprising 16 electrodes. Five features were extracted from each of the differential signals. An MLR model was used, together with a leave-one-out validation method, to define the uncertainty on the quantification of Manganese in sub-ppm concentration range. This made it possible to accurately recognize different classes of liquids in short times, thanks to the regression models and a well-defined reference solution.

Computerized systems and devices can be suitably designed for implementing embodiments of the present invention as described herein. In that respect, it can be appreciated that the methods described herein are largely non-interactive and automated. In exemplary embodiments, the methods described herein can be implemented either in an interactive, a partly interactive, or a non-interactive system. The methods described herein can be implemented in software, hardware, or a combination thereof. In exemplary embodiments, the methods proposed herein are implemented in software, as an executable program, the latter executed by suitable digital processing devices. More generally, embodiments of the present invention can be implemented wherein virtual machines and/or general-purpose digital computers, such as personal computers, workstations, etc., are used.

For instance, FIG. 8 schematically represents a computerized unit 101 (e.g., a general- or specific-purpose computer forming part or all of the processing system 30), which may possibly interact with other, similar units, so as to be able to perform steps involved in the present methods.

In exemplary embodiments, in terms of hardware architecture, as shown in FIG. 8, each unit 101 includes at least one processor 105, and a memory 110 coupled to a memory controller 115. Several processors (CPUs, and/or GPUs) may possibly be involved in each unit 101. To that aim, each CPU/GPU may be assigned a respective memory controller, as known per se.

One or more input and/or output (I/O) devices 145, 150, 155 (or peripherals) are communicatively coupled via a local input/output controller 135. The input/output controller 135 can be coupled to or include one or more buses and a system bus 140, as known in the art. The input/output controller 135 may have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processors 105 are hardware devices for executing software instructions. The processors 105 can be any custom made or commercially available processor(s). In general, processors 105 may involve any type of semiconductor-based microprocessor (in the form of a microchip or chip set), or generally any device for executing software instructions.

The memory 110 typically includes volatile memory elements (e.g., random-access memory), and may further include nonvolatile memory elements. Moreover, the memory 110 may incorporate electronic, magnetic, optical, and/or other types of storage media. The unit further includes a long-term storage 120.

Software in memory 110 may include one or more separate programs, each of which comprises executable instructions for implementing logical functions. In the example of FIG. 8, instructions loaded in the memory 110 may include instructions arising from the execution of the computerized methods described herein in accordance with exemplary embodiments. The memory 110 may further load a suitable operating system (OS) 111. The OS 111 essentially controls the execution of other computer programs or instructions and provides scheduling, input-output control, file and data management, memory management, and communication control and related services.

Possibly, a conventional keyboard and mouse can be coupled to the input/output controller 135. Other I/O devices 140-155 may be included. The computerized unit 101 can further include a display controller 125 coupled to a display 130. Any computerized unit 101 will typically include a network interface or transceiver 160 for coupling to a network, to enable, in turn, data communication to/from other, external components, e.g., other units 101.

The network transmits and receives data between a given unit 101 and other devices (not depicted). The network may possibly be implemented in a wireless fashion, e.g., using wireless protocols and technologies. The network may notably be a fixed wireless network, a wireless local area network (LAN), a wireless wide area network (WAN), a personal area network (PAN), a virtual private network (VPN), an intranet or other suitable network system and includes equipment for receiving and transmitting signals. Preferably though, this network should allow very fast message passing between the units.

The network can also be an IP-based network for communication between any given unit 101 and any external unit, via a broadband connection. In exemplary embodiments, network can be a managed IP network administered by a service provider. Besides, the network can be a packet-switched network such as a LAN, WAN, Internet network, an Internet of things network, etc.

The present invention can thus be embodied as a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, systems, and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or diagram block or blocks.

The computer readable program instructions may also be loaded onto a computer, other programmable data processing apparatus, or other device to cause a series of operational steps to be performed on the computer, other programmable apparatus, or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions demonstrated in the blocks may occur out of the order demonstrated in the Figures. For example, two blocks shown in succession may, in fact, be executed substantially concurrently, or the blocks may sometimes be executed in the reverse order, depending upon the functionality involved. It will also be demonstrated that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the present invention has been described with reference to a limited number of embodiments, variants, and the accompanying drawings, it will be understood by those skilled in the art that various changes may be made, and equivalents may be substituted without departing from the scope of the present invention. In particular, a feature (device-like or method-like) recited in a given embodiment, variant or shown in a drawing may be combined with or replace another feature in another embodiment, variant, or drawing, without departing from the scope of the present invention. Various combinations of the features described in respect of any of the above embodiments or variants may accordingly be contemplated, that remain within the scope of the appended claims. In addition, many minor modifications may be made to adapt a particular situation or material to the teachings of the present invention without departing from its scope. Therefore, it is intended that the present invention not be limited to the particular embodiments disclosed, but that the present invention will include all embodiments falling within the scope of the appended claims. In addition, many other variants than explicitly touched above can be contemplated.

What is claimed is:

1. A computer-implemented method comprising:
    obtaining, by one or more computer processors, one or more time-dependent signals with one or more sensor pairs in a sensing system, respectively, wherein each of the one or more time-dependent signals are obtained as a differential signal of a respective pair of the one or more sensor pairs by successively sensing a reference liquid and each liquid in a set of liquids to be characterized with the respective pair, wherein the reference liquid is selected to be a center of a plurality of steady-state values associated with each liquid in the set of liquids;
    extracting, by one or more computer processors, one or more sets of features from one or more portions of the one or more time-dependent signals, respectively, each of the one or more portions including a signal portion obtained while sensing each liquid in the set of liquids with said respective pair, wherein the one or more sets of features include an average of signal portions with respect to the reference liquid; and
    characterizing, by one or more computer processors, each liquid in the set of liquids based on the one or more extracted sets of features.

2. The computer-implemented method of claim 1, wherein extracting the one or more sets of features for each liquid in the set of liquids, further comprising:
    the signal portion of each of the one or more time-dependent signals includes a transient signal response obtained due to a transition from sensing the reference liquid to sensing each liquid in the set of liquids with the respective pair of the one or more sensor pairs; and
    each of the one or more sets of features extracted includes at least one transient feature.

3. The computer-implemented method of claim 2, wherein extracting the one or more sets of features for each liquid in the set of liquids, further comprising:
    the signal portion of each of the one or more time-dependent signals further includes a steady-state signal response obtained at an end of the transient signal response; and each of the one or more sets of features extracted further includes at least one steady-state feature.

4. The computer-implemented method of claim 1, wherein:
    each of the one or more time-dependent signals is obtained by further sensing the reference liquid again after having successively sensed the reference liquid and each liquid in the set of liquids with said respective pair;
    the signal portion of each of the one or more time-dependent signals includes a further transient signal response obtained due to a transition from sensing each liquid in the set of liquids to sensing said reference liquid again with the respective pair of the one or more sensor pairs; and
    each of the one or more extracted sets of features includes at least one further transient feature of the further transient signal response.

5. The computer-implemented method of claim 2, wherein the sensors are potentiometric sensors and each of the one or more time-dependent signals is obtained as a differential, potentiometric signal.

6. The computer-implemented method of claim 5, wherein:
    the one or more extracted sets of features from each of the one or more portions for each liquid in the set of liquids include two features, the latter consisting of:
        a feature obtained from a maximum voltage variation in the transient signal response, with respect to a reference value obtained by sensing the reference liquid with said respective pair; and
        a feature obtained from a slope of the transient signal response.

7. The computer-implemented method of claim 6, wherein:
    at extracting the one or more sets of features for each liquid in the set of liquids, the signal portion of each of the one or more time-dependent signals further includes a steady-state signal response obtained at an end of the transient signal response and each extracted set of features further includes, for each liquid in the set of liquids and for each of the one or more sets, three features, the latter respectively obtained from:
        a final absolute voltage value of the steady-state signal response;
        a final relative voltage value of the steady-state signal response; and an average of a complete signal response with respect to said reference value, the complete signal response including the transient signal response and the steady-state signal response.

8. The computer-implemented method of claim 5, wherein the sensors are designed to electrochemically interact with each liquid in the set of liquids.

9. The computer-implemented method of claim 5, wherein the sensing system includes an array of the sensors, the array designed so as to allow each liquid in the set of liquids to be simultaneously sensed by the one or more sensor pairs and the one or more time-dependent signals are simultaneously obtained for each liquid in the set of liquids, by simultaneously sensing each liquid in the set of liquids with the one or more sensor pairs.

10. The computer-implemented method of claim 1, further comprising:
selecting, by one or more computer processors, the reference liquid for it to be intermediate between each liquid in the set of liquids, with respect to one or more properties.

11. The computer-implemented method of claim 10, wherein the one or more properties includes one or more voltage signal response values of the signal responses obtained with one or more of the one or more sensor pairs and the one or more voltage signal response values include one or more of a steady-state voltage signal response value, an average voltage signal response value, and a maximal voltage signal response value.

12. The computer-implemented method of claim 10, further comprising:
prior to selecting the reference liquid, obtaining, by one or more computer processors, one or more signal responses for each liquid in the set of liquids, including the reference liquid, which is not identified as such yet, such that the reference liquid can be selected based on the one or more signal responses obtained.

13. The computer-implemented method of claim 1, wherein the one or more pairs of sensors are designed such that each of the resulting one or more time-dependent signals is linearly independent of remaining time-dependent signals.

14. The computer-implemented method of claim 1, wherein each liquid in the set of liquids is characterized so as to classify each liquid.

15. The computer-implemented method of claim 1, wherein each liquid in the set of liquids is characterized so as to quantify one or more properties thereof.

16. The computer-implemented method of claim 15, wherein each liquid in the set of liquids is an aqueous mixture of ions and is characterized so as to quantify concentrations of one or more ions therein.

17. The computer-implemented method of claim 1, wherein each liquid in the set of liquids is characterized using a cognitive model trained based on labelled examples by feeding the one or more sets of features obtained for each liquid in the set of liquids to the trained model for it to produce an inference.

18. The computer-implemented method of claim 17, wherein the cognitive model includes one or more regression models.

19. The computer-implemented method of claim 18, wherein the cognitive model includes both a linear regression model and a nonlinear regression model.

20. A system comprising:
a liquid storage including liquid containers adapted for storing respective liquids including a reference liquid and a set of liquids to be characterized;
a sensing system having a plurality of sensors arranged in one or more sensor pairs, wherein each of the one or more sensor pairs are configured to produce a differential signal, in operation and the sensing system and the liquid storage system are jointly configured to allow the sensing system to perform a plurality of sensing cycles, whereby, during each sensing cycle in the plurality of sensing cycles, each of the one or more sensor pairs successively senses the reference liquid and a liquid in the set of liquids to be characterized, so as to obtain one or more time-dependent signals as differential signals for each liquid in the set of liquids to be characterized, in operation, wherein the reference liquid is selected to be a center of a plurality of steady-state values associated with each liquid in the set of liquids; and
a processing system, which is connected to the sensing system to access the one or more time-dependent signals obtained, in operation, and is further configured to:
extract, for each liquid in the set of liquids, one or more sets of features from one or more portions of the one or more time-dependent signals accessed, respectively, each of the one or more portions including a signal portion obtained while sensing each liquid in the set of liquids with said respective pair, in operation, wherein the one or more sets of features include an average of signal portions with respect to the reference liquid; and
characterize each liquid in the set of liquids based on the one or more extracted sets of the one or more features.

21. The system of claim 20, wherein the sensing system comprises an array of the plurality of sensors, the array designed to allow the sensing system to simultaneously sense a liquid via the one or more sensor pairs, so as to simultaneously obtain the one or more time-dependent signals m at each of the m sensing cycles.

22. The system of claim 21, wherein the sensing system comprises:
a probe comprising said array of the plurality of sensors; and
a housing having an external surface, the latter including both a first surface portion and a second surface portion, wherein the housing is designed to maintain the probe so as for the probe to protrude from the second surface portion and thereby extend outside the housing, opposite to said first surface portion, thereby defining a gap between the first surface portion of the housing and a portion of a lateral surface of the probe and the gap has an open end and a closed end, the latter defined by the second surface portion of the housing.

23. The system of claim 21, wherein the plurality of sensors are potentiometric sensors, whereby each of the one or more time-dependent signals is obtained as a differential, potentiometric signal, in operation.

24. The system of claim 21, wherein the liquid storage is a turntable platform, adapted to rotate the containers in a plane; and the array is mounted on a linear displacement stage, adapted to move the array of the plurality of sensors perpendicularly to that plane.

25. A computer program product comprising:
one or more computer readable storage media and program instructions stored on the one or more computer readable storage media, the stored program instructions comprising:
program instructions to provide a set of liquids including a reference liquid and m liquids to be characterized, where $m \geq 2$, and a sensing system with N sensors arranged in n sensor pairs, where $N \geq 2$ and $n \geq 1$; and
for each liquid of the m liquids:
  program instructions to obtain n time-dependent signals with the n sensor pairs, respectively, wherein each of the n time-dependent signals is obtained as a differential signal of a respective pair of the n sensor pairs by successively sensing the reference liquid and said each liquid with said respective pair, wherein the reference liquid is selected to be a center of a plurality of steady-state values associated with each liquid in the set of liquids;
  program instructions to extract n sets of k features from n portions of the n time-dependent signals, respectively, where $k \geq 1$, each of the n portions including a signal portion obtained while sensing said each liquid with said respective pair, wherein the n sets of k features include an average of signal portions with respect to the reference liquid; and
  program instructions to characterize said each liquid based on the n sets of k features extracted therefor.

* * * * *